US012741139B2

(12) United States Patent
Becker et al.

(10) Patent No.: US 12,741,139 B2
(45) Date of Patent: Sep. 22, 2026

(54) IMPLANTABLE MEDICAL LEADS, SYSTEMS, AND RELATED METHODS WITH STRUCTURES FOR AIDING LEAD IMPLANTATION

(71) Applicant: MEDTRONIC, INC., Minneapolis, MN (US)

(72) Inventors: Damian M. Becker, Columbia Heights, MN (US); Haitao Zhang, Maple Grove, MN (US); Victor R. Hernandez, Humacao, OR (US); Jayesh Patel, Maple Grove, MN (US); Chandrasekhar Ramasubramanian Rajagopalan, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 632 days.

(21) Appl. No.: 18/113,503

(22) Filed: Feb. 23, 2023

(65) Prior Publication Data

US 2023/0364416 A1 Nov. 16, 2023

Related U.S. Application Data

(60) Provisional application No. 63/340,639, filed on May 11, 2022.

(51) Int. Cl.
*A61N 1/05* (2006.01)
*B29C 45/14* (2006.01)

(52) U.S. Cl.
CPC ............. *A61N 1/0551* (2013.01); *A61N 1/05* (2013.01); *A61N 1/0529* (2013.01); *A61N 1/0556* (2013.01); *A61N 1/0558* (2013.01); *B29C 45/14344* (2013.01); *B29C 45/14639* (2013.01)

(58) Field of Classification Search
CPC .. A61N 1/0551; A61N 1/0529; A61N 1/0556; A61N 1/0558; A61N 1/05; B29C 45/0001; B29C 45/14344; B29C 45/14639; B29C 45/1671
See application file for complete search history.

(56) References Cited

U.S. PATENT DOCUMENTS

| | | | | |
|---|---|---|---|---|
| 2010/0179562 A1* | 7/2010 | Linker | A61N 1/0551 607/117 |
| 2020/0338354 A1* | 10/2020 | Bolea | A61N 1/0529 |
| 2021/0045644 A1* | 2/2021 | Kramer | A61M 25/0147 |
| 2022/0355102 A1* | 11/2022 | Au | A61N 1/0556 |

* cited by examiner

*Primary Examiner* — Pamela M. Bays
(74) *Attorney, Agent, or Firm* — Shumaker & Sieffert, P.A.

(57) ABSTRACT

Implantable medical leads include at least one of a polymeric stylet tube and/or a distal backfill material that is softer than is conventional at least in the area where a stylet bend will cause a distal bend in the lead. The polymeric stylet tube provides for improved torsional and column stiffness during insertion while the softer distal backfill material reduces a whipping action to increase the steerability and control of the lead during insertion. The softer backfill material may be provided alone or in combination with a harder distal backfill material. The softer backfill material may be provided as an insert that is encapsulated by the harder distal back fill material or may be provided as a backfill material that exists in a position adjacent to the harder backfill material.

13 Claims, 11 Drawing Sheets

IMPLANTABLE MEDICAL LEADS, SYSTEMS, AND RELATED METHODS WITH STRUCTURES FOR AIDING LEAD IMPLANTATION

RELATED APPLICATIONS

This application claims priority to U.S. Prov. Application No. 63/340,639, filed on May 11, 2022, and titled IMPLANTABLE MEDICAL LEADS, SYSTEMS, AND RELATED METHODS WITH STRUCTURES FOR AIDING LEAD IMPLANTATION, which is incorporated by reference herein.

TECHNICAL FIELD

Embodiments relate to implantable medical leads, systems, and methods. More particularly, embodiments relate to structures of the leads and systems that aid with the implantation of implantable medical leads.

BACKGROUND

Implantable medical systems are used to provide therapy to a patient. The implantable medical system may include an implantable medical device such as a device capable of producing electrical stimulation signals and/or sensing physiological signals. The implantable medical device is typically implanted in a location of convenience for the condition of the patient to be treated. For instance, a patient suffering from pain involving the spine may have an implantable medical device implanted in the upper buttocks region. The implantable medical lead is then implanted by being inserted into the patient by being pushed and steered until a distal end of the implantable medical lead reaches the target location for the stimulation therapy to be applied. The proximal end of the lead is connected to the implantable medical device or in some situations a lead extension that is connected to the implantable medical device.

The placement of the distal end of the lead at the proper location within the patient is crucial to the success of the stimulation therapy. Accordingly, the ability of the implantable medical lead to be pushed and steered during insertion is of utmost importance to ensure the lead can be effectively inserted. When inserting the lead, it may be necessary to overcome obstacles and small clearances within the body that block or constrict the pathway that the lead must take to reach the target location. Thus, the lead needs to have sufficient steerability to avoid the obstacles and sufficient pushability to overcome friction caused by tight clearances.

The lead is typically constructed of polyurethane or similar relatively flexible polymeric material that allows the lead to bend between the target location and the location of the implantable medical device. While this allows the lead to follow a desired pathway, this flexibility hinders the ability of the lead 106 to avoid kinking when being pushed. One solution is to include a metal coil within the polyurethane tube. However, this solution has drawbacks. The metal coil is a significant additional cost. Furthermore, including the metal coil may result in an increased outside diameter of the coil and therefore the lead that is larger than desired while still not achieving the desired level of torsional stiffness.

A stylet is typically placed in the lead with a bent end that allows the stylet to steer the direction that the lead travels during insertion. One manner of using a stylet is to utilize the metal coil to define a stylet lumen. However, as noted above, the metal coil has drawbacks. Furthermore, the conventional lead is not always adequately responsive to the stylet during attempts to steer the lead. Axial rotation applied to the proximal end of the stylet by the clinician causes the stylet to axially rotate which changes the direction that the bent distal end points. This also changes the direction the distal tip of the lead is pointing which in turn controls the direction of movement of the lead as it is being pushed.

While some degree of steering may be possible, the conventional lead may be susceptible to a whipping action that causes the distal end to not maintain the intended direction of the bend caused by the bend of the stylet as the stylet rotates the bend to point in a different direction. This whipping action negatively impacts the ability to control and steer the lead during insertion since the distal end of the lead does not maintain the intended direction.

SUMMARY

Embodiments address one or more of the issues above and others by providing an implantable medical lead with one or more structures that aid in the insertion of the lead. For instance, embodiments of the implantable medical lead may be provided with a polymeric tube with a higher durometer rating, and thus a greater torsional stiffness, than the outer lead body to provide the stylet lumen and increase the pushability of the lead. As another example, embodiments of the implantable medical lead may include a backfill material in the distal end that is softer than the backfill material of conventional leads to reduce the whipping action that occurs at the distal end during rotation of the bent distal tip of the stylet within the stylet lumen of the lead.

Embodiments provide an implantable medical lead that includes a lead body defining a first lumen, the lead body comprising a first material. The lead includes a polymeric tube that is located within the first lumen for at least a portion of a length of the first lumen, the tube defining a second lumen, the tube comprising a second material having a higher durometer rating than the first material. The lead includes at least one proximal connector located on a proximal end of the lead body where the tube is present. The lead includes at least one distal electrode located on a distal end of the lead body where the tube is present. The lead also includes at least one conductor interconnecting the at least one proximal connector and the at least one distal electrode.

Embodiments provide an implantable medical lead that includes a lead body defining a first lumen, the lead body comprising a first material. The lead includes at least one proximal connector located on a proximal end of the lead body. The lead includes at least one distal electrode located on a distal end of the lead body. The lead includes a first backfill material within the lumen and present at the at least one distal electrode and having a durometer lower than 100 on the Shore A hardness scale. The lead also includes at least one conductor interconnecting the at least one proximal connector and the at least one distal electrode.

Embodiments provide an implantable medical lead that includes a lead body defining a first lumen, the lead body comprising a first material. The lead includes at least one proximal connector located on a proximal end of the lead body. The lead includes at least one distal electrode located on a distal end of the lead body. The lead includes a first backfill material within the lumen and present at the at least one distal electrode. The lead includes a second backfill material within the lumen and present proximally of the first backfill material, wherein the first backfill material has a softer durometer rating than the second backfill material.

The lead also includes at least one conductor interconnecting the at least one proximal connector and the at least one distal electrode.

Embodiments provide a method of constructing a lead that involves forming a lead body that comprises a first material about a polymeric tube so that the lead body has a proximal end and a distal end, the polymeric tube defining a lumen and the polymeric tube comprising a second material having a higher durometer rating than the first material. The method further involves providing the lead body with at least one proximal connector on the proximal end of the lead body, at least one distal electrode on the distal end of the lead body, and at least one electrical conductor interconnecting the at least one proximal connector to the at least one distal electrode.

Embodiments provide a method of constructing a lead that involves providing a lead body having a proximal end, a distal end, with at least one proximal connector on the proximal end, at least one distal electrode on the distal end, and at least one electrical conductor interconnecting the at least one proximal connector to the at least one distal electrode, the lead body defining a lumen. The method further involves positioning a first material into the lumen at the at least one distal electrode, the first material having a durometer rating lower than 100 on the Shore A hardness scale.

Embodiments provide a method of constructing a lead that involves providing a lead body having a proximal end, a distal end, with at least one proximal connector on the proximal end, at least one distal electrode on the distal end, and at least one electrical conductor interconnecting the at least one proximal connector to the at least one distal electrode, the lead body defining a lumen. The method involves positioning a first material into the lumen at the at least one distal electrode. The method further involves backfilling a second material into the lumen proximal of the first material, wherein the first material has a softer durometer rating than the second material.

DETAILED DESCRIPTION

Embodiments provide implantable medical leads and related systems and methods that include examples of structures that aid in the insertion of the lead during lead implantation. Embodiments provide examples of stylet tubes that provide stiffening to aid in pushability of the lead during insertion. Embodiments provide examples of one or more distal fill materials that aid in the steering of the lead during insertion.

Figure 1:
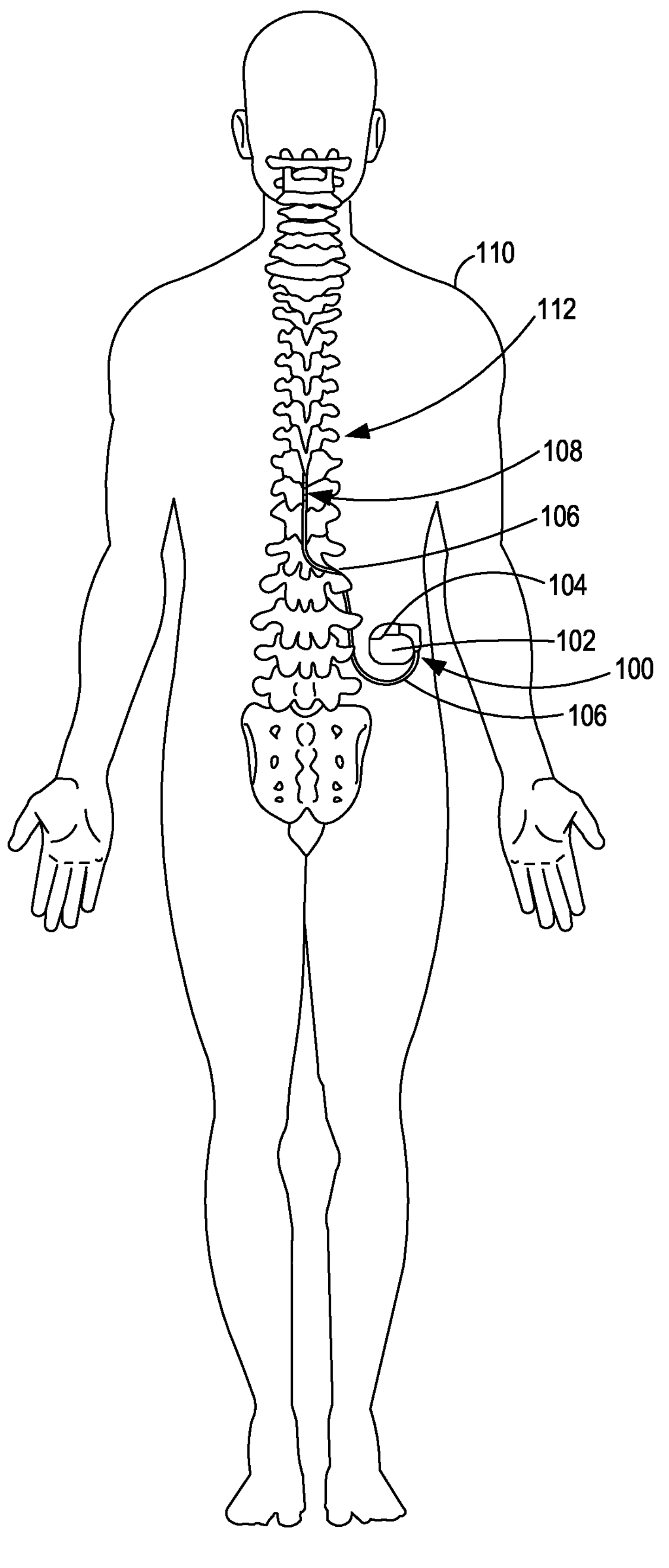
FIG. 1 shows an example of an implantable medical system implanted within a patient.

FIG. 1 shows an example of an implantable medical system 100 implanted into a patient 110. In this example, the implantable medical system 100 is a neurostimulation system providing electrical stimulation therapy within the spine 112, typically within the epidural space. It will be appreciated that the implantable medical system 100 may alternatively be used for other therapies in other areas of the body of the patient 100. The implantable medical system 100 includes an implantable medical device 102 having a header portion 104 and an implantable medical lead 106 having a proximal end inserted into the header portion 104. In this example, the implantable medical lead 106 has been inserted into the patient and with a distal end of the lead 106 being steered to a target site within the spinal region of the patient 110. Distal electrodes 108 on the distal end of the lead 106 are then in position to deliver the stimulation signals being generated by the device 102 to the body tissue.

Figure 2:
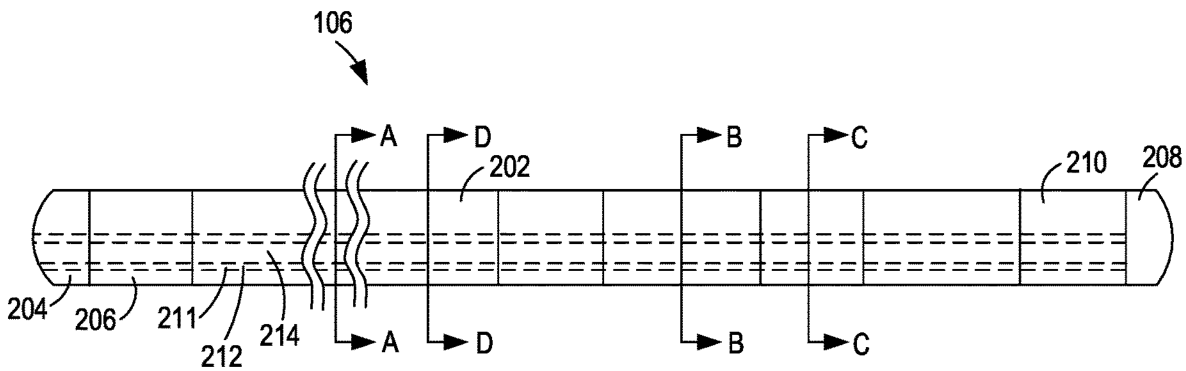
FIG. 2 shows an example of an implantable medical lead of the implantable medical system that includes a stylet tube.

FIG. 2 shows an example of the implantable medical lead 106 including a lead body 202, a proximal end 204, and a distal end 208. Proximal connectors 206 are located on the proximal end 204 for purposes of creating an electrical connection with the header portion 104 of the device 102. Electrical conductors within the lead body 202 that are not visible in FIG. 2 are present to electrically interconnect the proximal connectors 206 to distal electrodes 210 located on the distal end 208.

The lead 106 also includes a stylet tube 212 that provides a stylet lumen 214. In this example of FIG. 2, the stylet tube 212 extends from proximal tip to distal tip with the stylet lumen 214 being open to the ambient on the proximal tip to allow ingress of a stylet. To provide potential cost reductions and potentially reduce manufacturing defects associated with a metal coil stylet tube, the stylet tube 212 in FIG. 2 may be made of a polymeric material. To provide the desired pushability of the lead 106 and resist kinking, the polymeric material of the stylet tube 212 may have a durometer rating that is greater than that of the relatively softer and more flexible material of the lead body 202, may have a tensile strength greater than that of the material of the lead body 202, and/or may have an ultimate elongation less than that of the material of the lead body 202.

As a specific example, the lead body 202 may be constructed of a soft polyurethane with a hardness of less than 60 Shore D. Meanwhile, the tube 212 may be constructed of a polymer with a hardness of greater than 60 Shore D. For instance, the stylet tube 212 may be constructed from one or more polymers such as polyimide, acrylonitrile butadiene styrene, polyvinylidene fluoride, polycarbonate, polyethylene terephthalate, cellulose acetate, or polyvinyl chloride.

Figure 3:
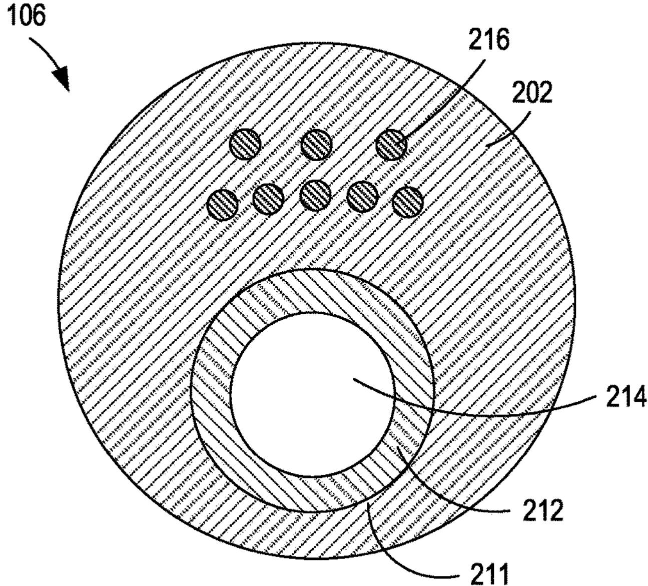
FIG. 3 shows a lateral cross-sectional view of the implantable medical lead taken through line A-A of FIG. 2.

FIG. 3 shows a lateral cross-sectional view taken through line A-A of FIG. 2 where both the lead body 202 and the stylet tube 212 with lumen 214 can be seen, with the stylet tube 212 being present within a lumen 211 formed by the lead body 202. Line A-A is present in an area that is distal of the most distal proximal connector 204 and proximal of the most proximal distal electrode 210. As shown in FIG. 3, conductors 216 are also present and extend through the lead body 202 to electrically connect the proximal connectors 206 to the distal electrodes 210. As can be further seen in FIG. 3, the lead body 202 surrounds and contacts a complete circumference of the stylet tube 212 at the location of the line A-A while the stylet lumen 214 is present to allow the stylet to extend through the lead 106.

Figure 4:
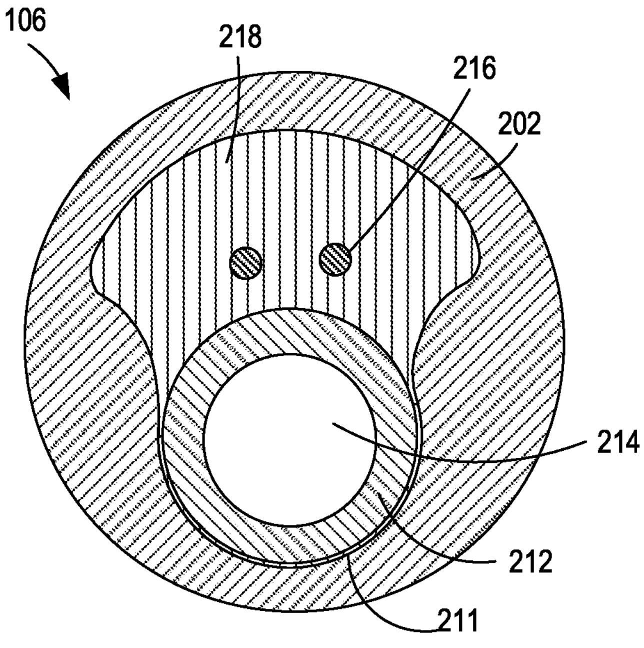
FIG. 4 shows a lateral cross-sectional view of a first example of a distal end of the implantable medical lead taken through line B-B of FIG. 2.

FIG. 4 shows a lateral cross-sectional view taken for a first example of the distal end of the lead 106 taken through line B-B of FIG. 2 where the distal bend occurs when the stylet is inserted. The area where the distal bend occurs when the bent stylet is inserted typically spans the two most distal electrodes, but it will be appreciated that the distal bend resulting from the bent stylet can span a different number of distal electrodes in some cases. Line B-B is in an area nearby the distal electrodes 210 where the lumen 211 formed by the lead body 202 that contains the stylet tube 212 has expanded to also accommodate a distal backfill material 218. At the location of line B-B, any conductors 216 that have not yet terminated at a distal electrode continue to extend through the backfill material 218.

The backfill material 218 may be of various types. For embodiments where the benefits of the polymeric stylet tube 212 are desired but whipping action of the distal end 208 is not a concern, then the stylet tube 212 may be the polymeric tube 212 discussed above while the backfill material 218 may be the conventional relatively hard epoxy backfill such as epoxy with a durometer rating of about 70 on the Shore D hardness scale. However, where whipping action at the distal end is a concern due to the need to steer the lead with a bent stylet, then the backfill material may be a softer material than the conventional epoxy backfill material at least in the area where the stylet bend will occur. The line B-B of FIG. 2 is present where the stylet bend will occur, and thus the backfill material 218 present at the line B-B may be the softer backfill material.

For leads 106 that include the softer material in the distal end 208 where the stylet bend is present to reduce the whipping action, the softer backfill material may have a lower durometer rating relative to the conventional epoxy. For instance, the softer backfill material may have a rating lower than 100 on the Shore A hardness scale. Some examples of the softer backfill material include softer epoxies and copolymers, silicones, polyurethanes (pre-polymerized), polyurethanes (in situ polymerized), and polyacrylates. Examples of applicable curing mechanisms for these softer backfill materials include thermal, moisture, and light/UV initiated cure chemistries. It will be appreciated that this softer backfill material may be used in embodiments of the lead 106 that include a conventional metal coil stylet tube or the polymeric stylet tube described above.

Figure 5:
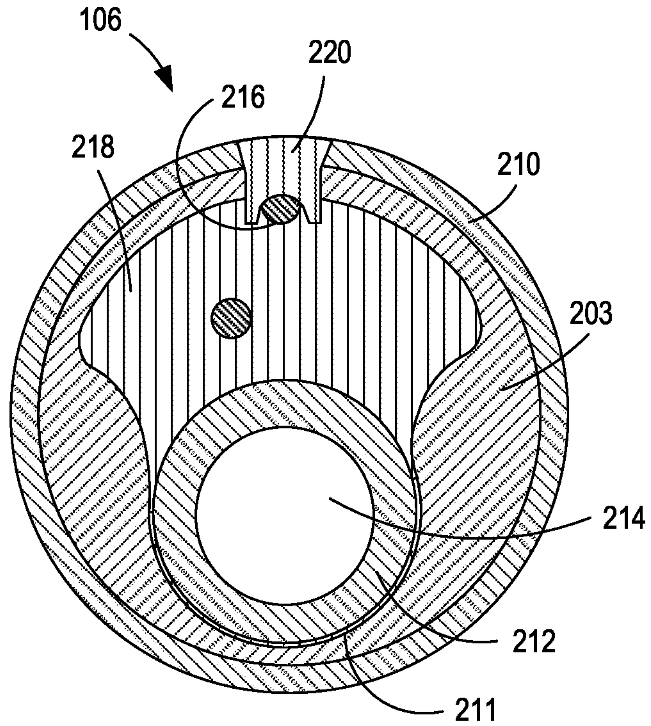
FIG. 5 shows a lateral cross-sectional view of the first example of the distal end of the implantable medical lead taken through line C-C of FIG. 2.

FIG. 5 shows a lateral cross-sectional view taken through line C-C of FIG. 2 which is taken through one of the distal electrodes 210 present on the distal end of the lead 106 where the distal bend occurs when the stylet is inserted. Here it can be seen that the lead body 202 is now present as a thinned down portion 203 that fits inside the ring formed by the distal electrode 210. The lumen 211 provided by the lead body 202 contains both the stylet tube 212 and the backfill material 218 as well as the remaining conductors. However, the conductor 216 intended for this particular electrode is captured by a crimp sleeve 220 that is also attached to the electrode 210 to complete an electrical connection from the conductor 216 to the electrode 210.

Figure 6:
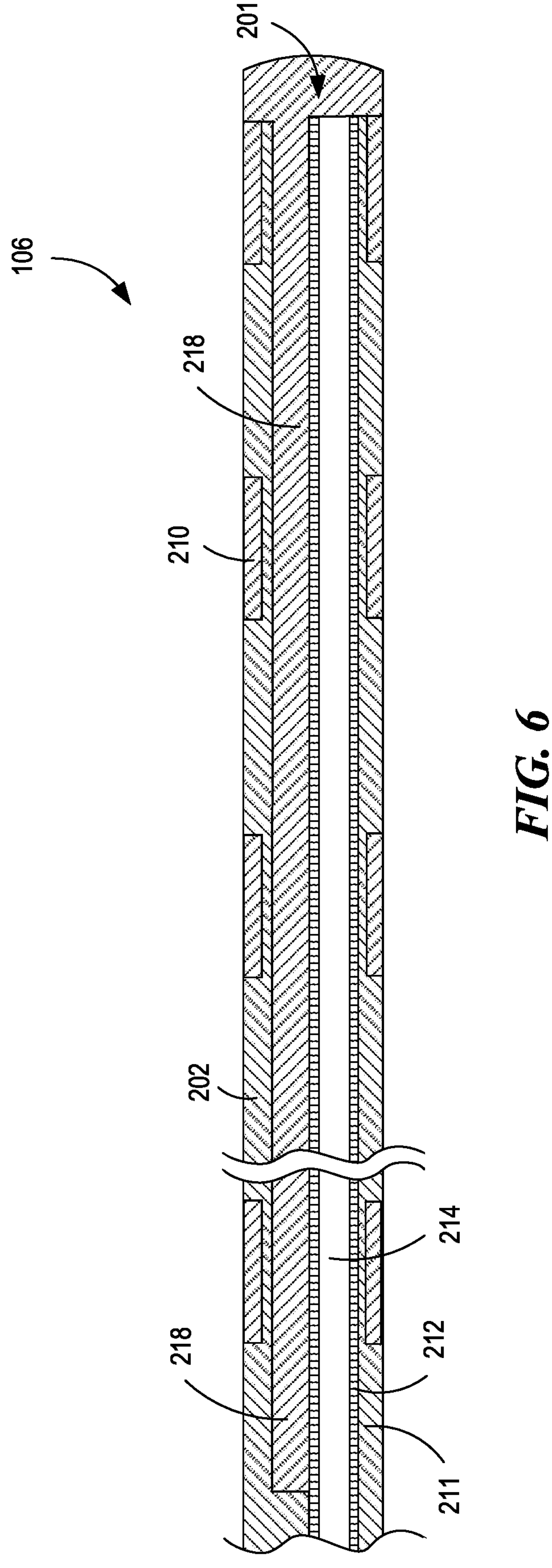
FIG. 6 shows a longitudinal cross-sectional view of the first example of the distal end of the implantable medical lead of FIG. 2 showing an example of a stylet tube and an example of a distal backfill material.

FIG. 6 shows a longitudinal cross-sectional view taken through the centerline of the lead body 202 and stylet tube 212 which may be the polymeric tube discussed above in some embodiments. In this example, it can be seen that the backfill material 218 extends from a point proximal of the most proximal electrode where the lumen 211 provided by the lead body 202 has expanded. The backfill material 218 continues distally to form the distal tip 201 of the lead 106. The backfill material 218 may be the softer backfill material discussed above in some embodiments and is adjacent the stylet tube 212.

Figure 7:
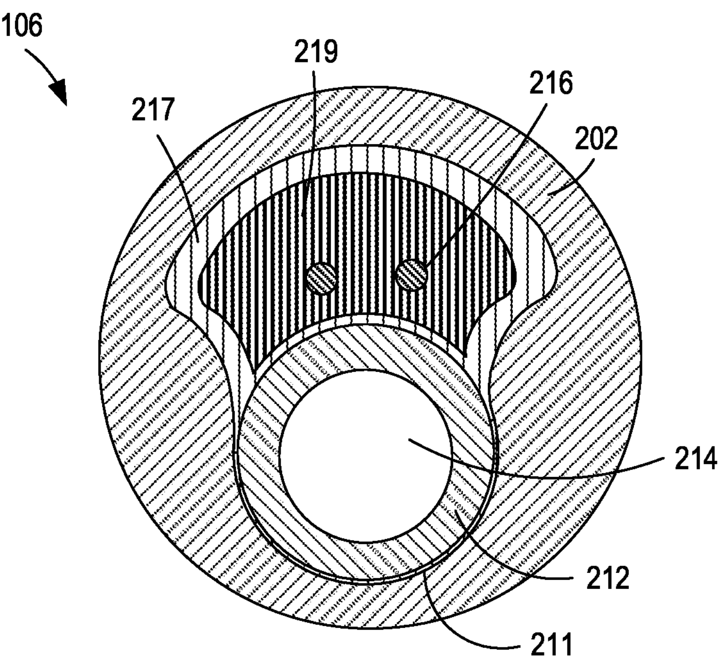
FIG. 7 shows a lateral cross-sectional view of a second example of the distal end of the implantable medical lead taken through line B-B of FIG. 2.

FIG. 7 shows a lateral cross-sectional view taken for a second example of the distal end of the lead 106 taken through line B-B of FIG. 2 where the distal bend occurs when the stylet is inserted. As previously stated, line B-B is in an area nearby the distal electrodes 210 where the lumen 211 formed by the lead body 202 that contains the stylet tube 212 has expanded to also accommodate distal backfill materials 217 and 219. The first distal backfill material 219 may an insert that is formed of the softer backfill material discussed above. The second distal backfill material 217 may be the conventional epoxy backfill discussed above when encapsulates the insert formed of the first distal backfill material 219. At the location of line B-B, any conductors 216 that have not yet terminated at a distal electrode continue to extend through the backfill material 218.

This second example provides a reduction of the whipping action by virtue of the insert formed of the first backfill material 219 being softer than the surrounding second backfill material 217 while encompassing the majority of the volume of the space where the backfill materials 217, 219 are present at least throughout the area where the distal bend occurs.

As previously discussed, the stylet tube 212 may be the polymeric tube discussed above in some embodiments so as to be used in combination with the first backfill material 219 forming the insert and the second backfill material 217 encapsulating the first backfill material 219. In other embodiments, the stylet tube 212 may be the conventional metal coil tube used in combination with the first backfill material 219 forming the insert and the second backfill material 217 encapsulating the first backfill material 219.

Figure 8:
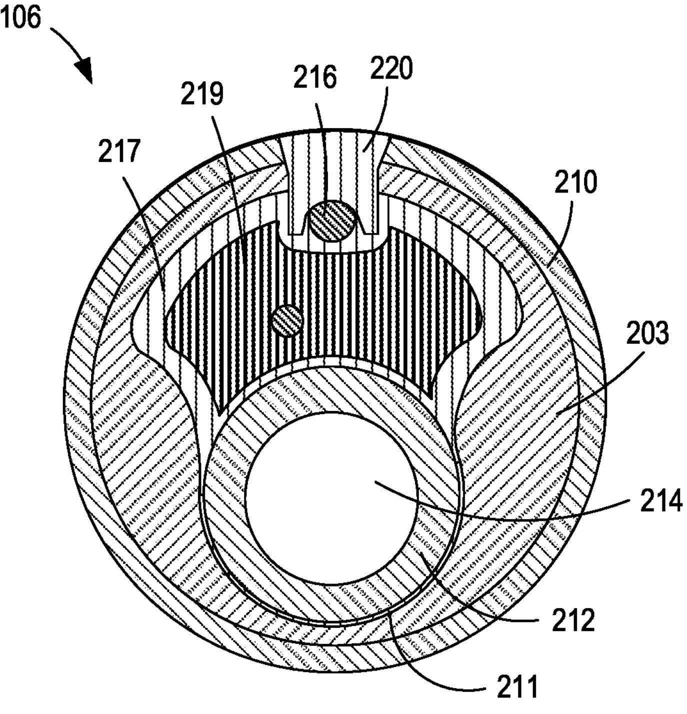
FIG. 8 shows a lateral cross-sectional view of the second example of the distal end of the implantable medical lead taken through line C-C of FIG. 2.

FIG. 8 shows a lateral cross-sectional view of the second example of the distal end of the lead 106 taken through line C-C of FIG. 2 which is taken through one of the distal electrodes 210 present on the distal end of the lead 106 where the distal bend is occurs when the stylet is present. Here it can again be seen that the lead body 202 is now present as a thinned down portion 203 that fits inside the ring formed by the distal electrode 210. The lumen 211 provided by the lead body 202 contains the stylet tube 212, the second backfill material 217, the first backfill material 219 forming the softer insert, and the remaining conductors. Conductor 216 that is intended for this particular electrode is captured by a crimp sleeve 220 that is also attached to the electrode 210 to complete an electrical connection from the conductor 216 to the electrode 210.

Figure 9:
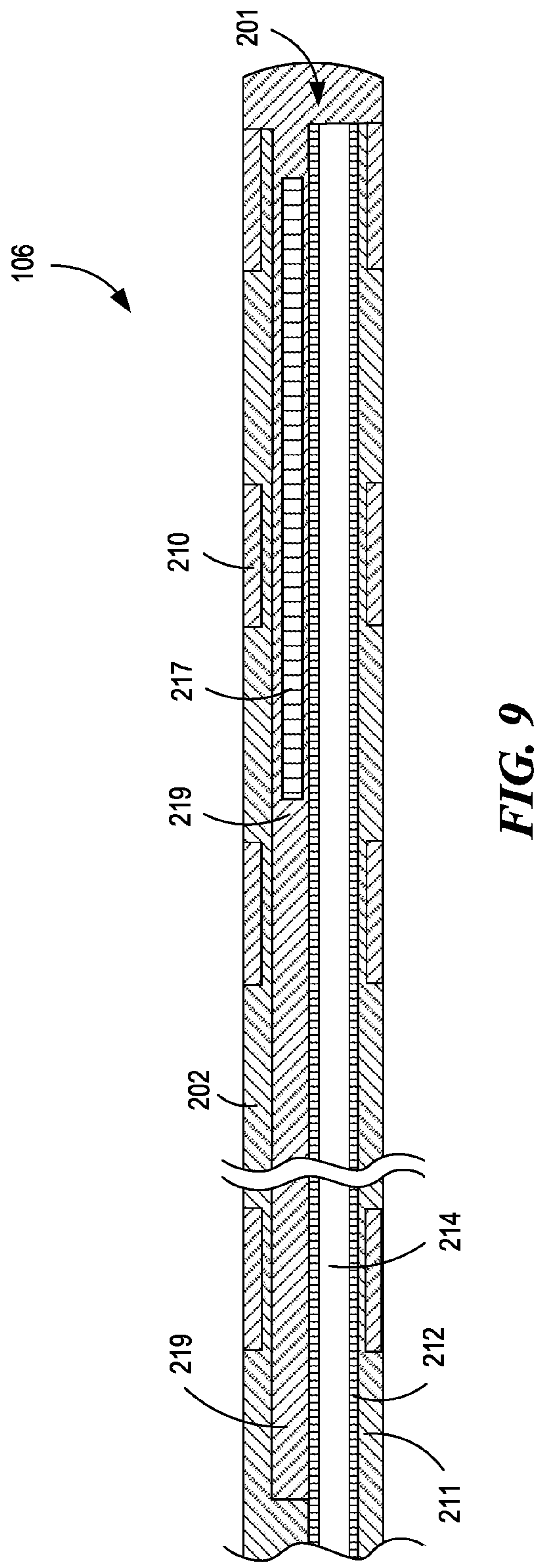
FIG. 9 shows a longitudinal cross-sectional view of the second example of the distal end of the implantable medical lead of FIG. 2 showing an example of a stylet tube and an example of a first distal backfill insert material and a second distal backfill material.

FIG. 9 shows a longitudinal cross-sectional view of this second example of the distal end of the lead 106 taken through the centerline of the lead body 202 and stylet tube 212 which again may be the polymeric tube discussed above in some embodiments. In this example, it can be seen that the insert created by the first backfill material 219 is present in the area spanning the first two most distal electrodes 210. It can be seen that the second backfill material 217 extends from a point proximal of the most proximal electrode where the lumen 211 provided by the lead body 202 has expanded and encapsulates the insert formed by the first backfill material 219. The second backfill material 217 continues distally beyond the insert formed by the first backfill material 219 to form the distal tip 201 of the lead 106.

Figure 10:
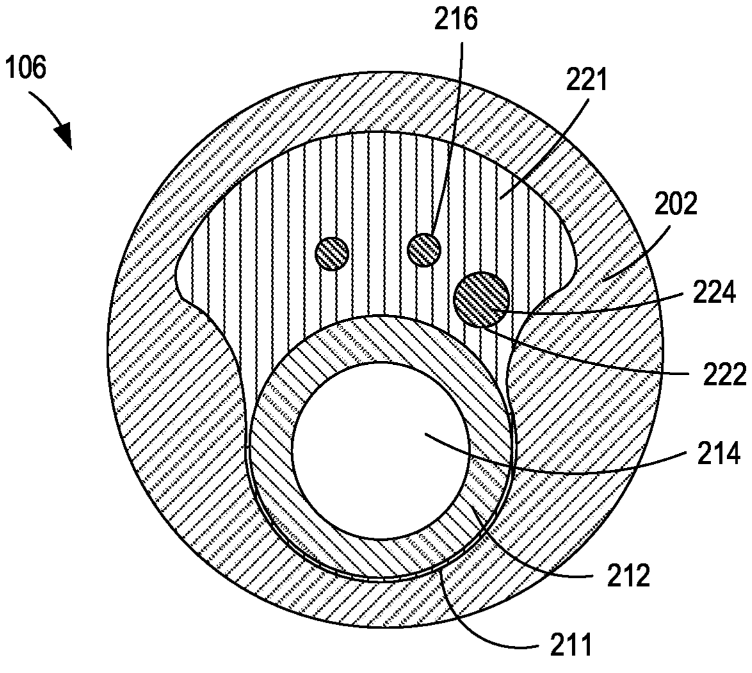
FIG. 10 shows a lateral cross-sectional view of a third example of the distal end of the implantable medical lead taken through line B-B of FIG. 2.

FIG. 10 shows a lateral cross-sectional view taken for a third example of the distal end of the lead 106 taken through line B-B of FIG. 2 where the distal bend occurs when the stylet is inserted. As previously stated, line B-B is in an area nearby the distal electrodes 210 where the lumen 211 formed by the lead body 202 that contains the stylet tube 212 has expanded to also accommodate distal backfill materials 221 and 224. The first distal backfill material 221 may fill the expanded lumen 211 created by the lead body 202, and the first distal backfill material 221 may be formed of the softer backfill material discussed above. The second distal backfill material 224 may be the conventional epoxy backfill discussed above. At the location of line B-B, any conductors 216 that have not yet terminated at a distal electrode continue to extend through the first backfill material 221. This third example provides a reduction of the whipping action by virtue of the first backfill material 221 being present at least throughout the area where the distal bend occurs.

The second distal backfill material 224 is present within a lumen 222 formed in the first backfill material 221 at line B-B. This is a result of the backfilling process discussed below in relation to FIG. 12. In a more proximal location, as indicated by line D-D of FIG. 2, the second backfill material 224 may fill the expanded lumen 211 of the lead body 202, as there is no need for the softer first backfill material 221 at line D-D since this point is proximal of where the distal bend will occur and does not impact the reduction of the whipping action. when encapsulates the insert formed of the first distal backfill material 219. The lateral cross-section at line D-D therefore looks like the lateral cross-section shown in FIG. 4 from the first example of the distal end where the second distal backfill material 224 of FIG. 10 is represented as backfill material 218.

As previously discussed, the stylet tube 212 may be the polymeric tube discussed above in some embodiments so as to be used in combination with the first backfill material 221 and the second backfill material 224 occupying space proximal of the first backfill material 221. In other embodiments, the stylet tube 212 may be the conventional metal coil tube used in combination with the first backfill material 221 and the second backfill material 224.

Figure 11:
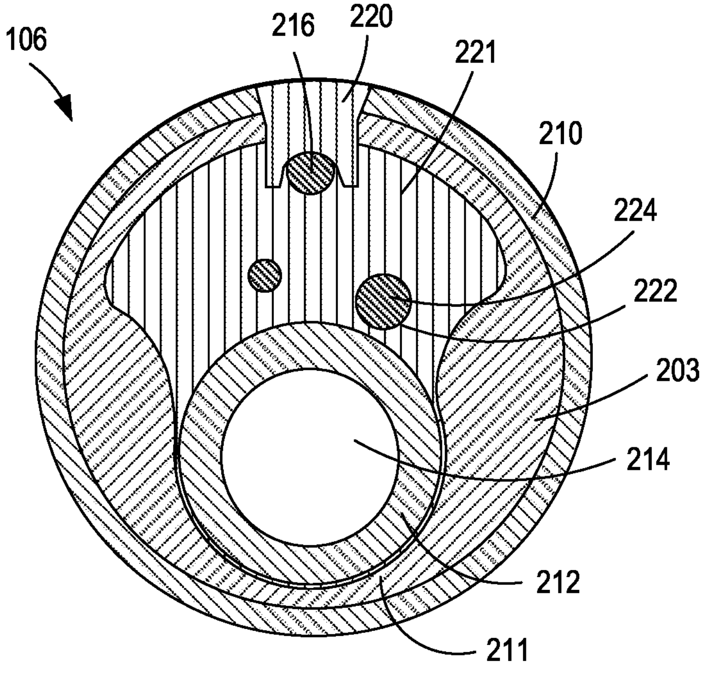
FIG. 11 shows a lateral cross-sectional view of the third example of the distal end of the implantable medical lead taken through line C-C of FIG. 2.

FIG. 11 shows a lateral cross-sectional view of the third example of the distal end of the lead 106 taken through line C-C of FIG. 2 which is taken through one of the distal electrodes 210 present on the distal end of the lead 106 where the distal bend is occurs when the stylet is present. Here it can again be seen that the lead body 202 is now present as a thinned down portion 203 that fits inside the ring formed by the distal electrode 210. The lumen 211 provided by the lead body 202 contains the stylet tube 212, the first backfill material 221, the second backfill material 224 within the lumen 211 of the first backfill material, and the remaining conductors. Conductor 216 that is intended for this particular electrode is captured by the crimp sleeve 220 that is also attached to the electrode 210 to complete an electrical connection from the conductor 216 to the electrode 210.

Figure 12:
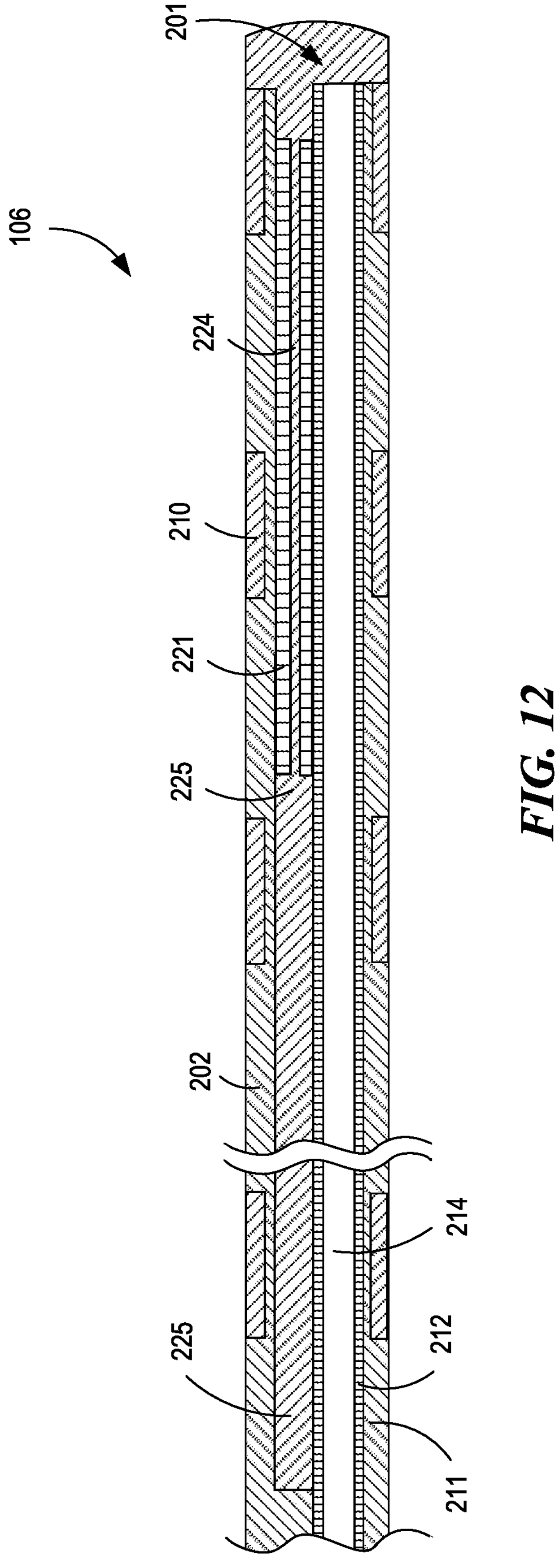
FIG. 12 shows a longitudinal cross-sectional view of the third example of the distal end of the implantable medical lead of FIG. 2 showing an example of a stylet tube and an example of a first distal backfill material and a second distal backfill material proximal.

FIG. 12 shows a longitudinal cross-sectional view of this third example of the distal end of the lead 106 taken through the centerline of the lead body 202 and stylet tube 212 which again may be the polymeric tube discussed above in some embodiments. In this example, it can be seen that the first backfill material 221 is present in the area spanning the first two most distal electrodes 210. It can be seen that the second backfill material 224 extends from a point proximal of the most proximal electrode where the lumen 211 provided by the lead body 202 has expanded up to the location of the first backfill material 221, then extends through the lumen 222 formed in the first backfill material 222 and continues beyond the electrodes 210 to then form the distal tip 201.

Figure 13:
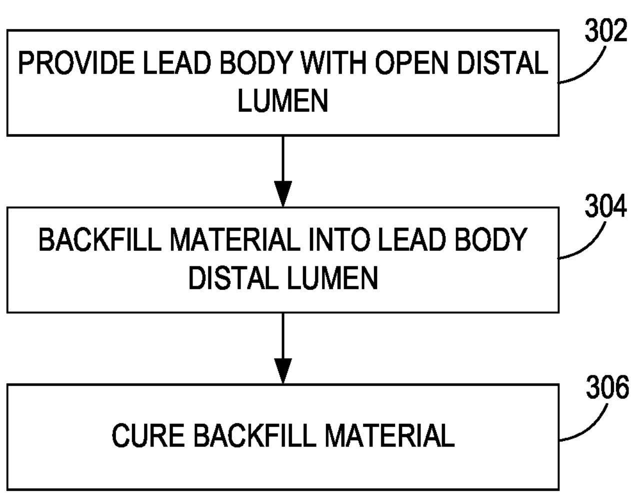
FIG. 13 shows an example of steps of a method to backfill a distal end of a lead.
Figure 14:
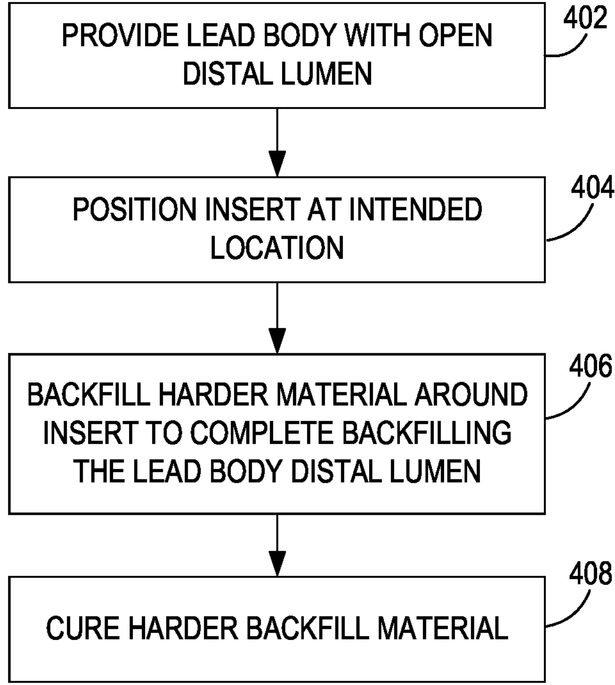
FIG. 14 shows an example of steps of a method to create backfill a distal end of a lead that includes a softer insert encapsulated by a harder material.
Figure 15:
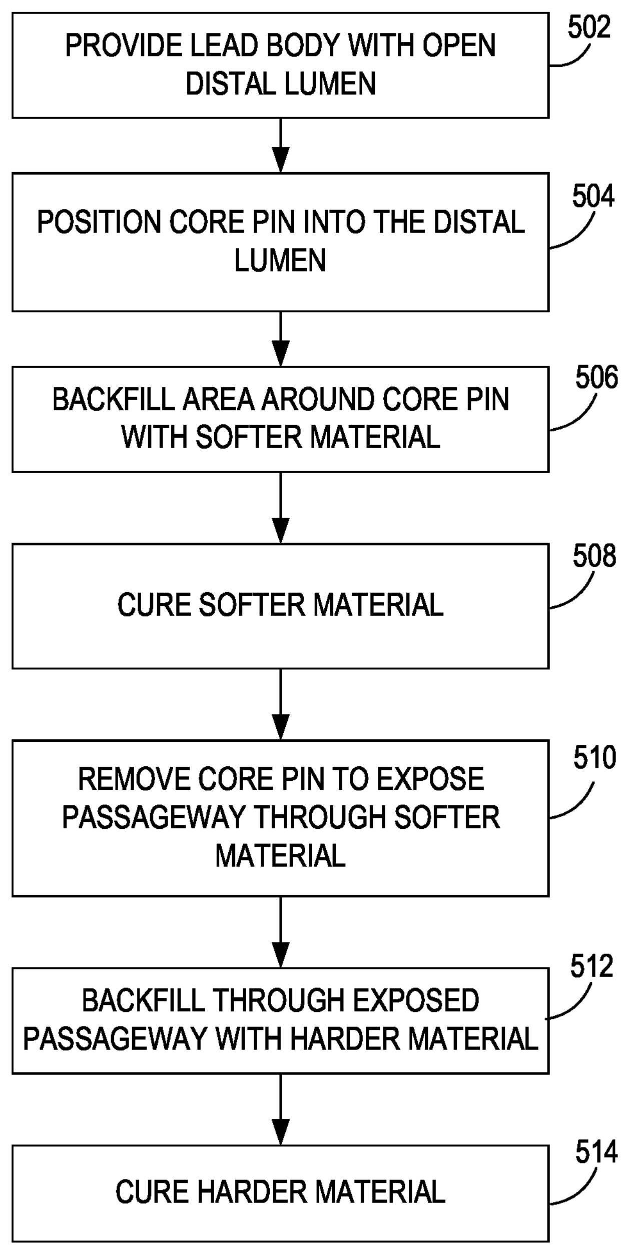
FIG. 15 shows an example of steps of a method to backfill a distal end of a lead that includes a softer backfill material and a subsequently positioned harder backfill material proximal, and distal in some cases, of the softer backfill material.

Methods for backfilling these distal end examples are shown in FIGS. 13-15. FIG. 13 shows the steps involved in backfilling the first example discussed above in relation to FIGS. 4-6. The method begins at a step 302 by providing a lead body having a proximal end, a distal end, with at least one proximal connector on the proximal end, at least one distal electrode on the distal end, and at least one electrical conductor interconnecting the at least one proximal connector to the at least one distal electrode. The lead body defines the lumen 211 at the distal end. The method continues by injecting the backfill material 218 into the lumen 211 of the lead body at a step 304. Here, the backfill material 218 may form the distal tip of the lead. The backfill material is then cured at a step 306 to complete the process.

FIG. 14 shows the steps involved in backfilling the second example discussed above in relation to FIGS. 7-9. The method begins at a step 402 by providing a lead body having a proximal end, a distal end, with at least one proximal connector on the proximal end, at least one distal electrode on the distal end, and at least one electrical conductor interconnecting the at least one proximal connector to the at least one distal electrode. The insert made of the softer first backfill material 219 is then positioned into the lumen 211 formed by the lead body 202 and in the area where the distal bend should occur at a step 404. This insert made of the first backfill material 219 has already been cured prior to insertion into the lumen 211 in this example. Then the remaining space within the lumen 211 of the lead body 202 is filled with the second backfill material 217 including filling any space proximal of the insert material 219 and forming the distal tip at a step 406. The second backfill material 217 is then cured at a step 408 to complete the process.

In other examples, the first backfill material may be backfilled before being cured, and the second backfill material may be first backfilled up to an area proximal of where the distal bend is to be located so that the backfilled first material may completely fill that area. The second backfill material may be vented and allowed to cure while the first backfill material is thereafter backfilled and also allowed to cure, with the second backfill material being used to create a robust distal tip. As an alternative, the first backfill material may be backfilled prior to any backfilling with the second backfill material, and this approach is described with reference to FIG. 15.

FIG. 15 shows the steps involve in backfilling the third example discussed above in relation to FIGS. 10-12. The method begins at a step 502 by providing a lead body having a proximal end, a distal end, with at least one proximal connector on the proximal end, at least one distal electrode on the distal end, and at least one electrical conductor interconnecting the at least one proximal connector to the at least one distal electrode. The method continues by inserting a core pin into the distal end of the lumen 211 created by the lead body 202 at step 504. The core pin may be coated with a material, such as Polytetrafluoroethylene (PTFE) that does not bond to the softer first backfill material. Then, the area around the core pin within the lumen 211 of the lead body 202 is backfilled with the softer first backfill material 221 at a step 506. The first backfill material 221 is cured at a step 508. Then, the core pin is removed at a step 510. By first backfilling with first backfill material 221 prior to other backfill material, this allows the volume intended to be backfilled by the first backfill material 221 to be completely backfilled with the first backfill material 221 without interference from any other backfill material that might otherwise be present in the space intended for the backfill material 221. However, because other backfill material is intended to be located proximal of the first backfill material 221, the passageway must be created through the backfill material 221 with the core pin.

Once the core pin has been removed, the method transitions to backfilling with the harder second backfill material 224 at a step 512. The second backfill material 224 is backfilled through the passageway or lumen 222 present in the cured first backfill material 221 created by the prior presence of the core pin to backfill the void that is proximal of the first backfill material 221 at a step 512. The second backfill material 224 may also backfilled to form the distal tip in the area distal of the first backfill material 221 at this step 512. The second backfill material 224 is then cured at a step 514 to complete the process.

Figure 16:
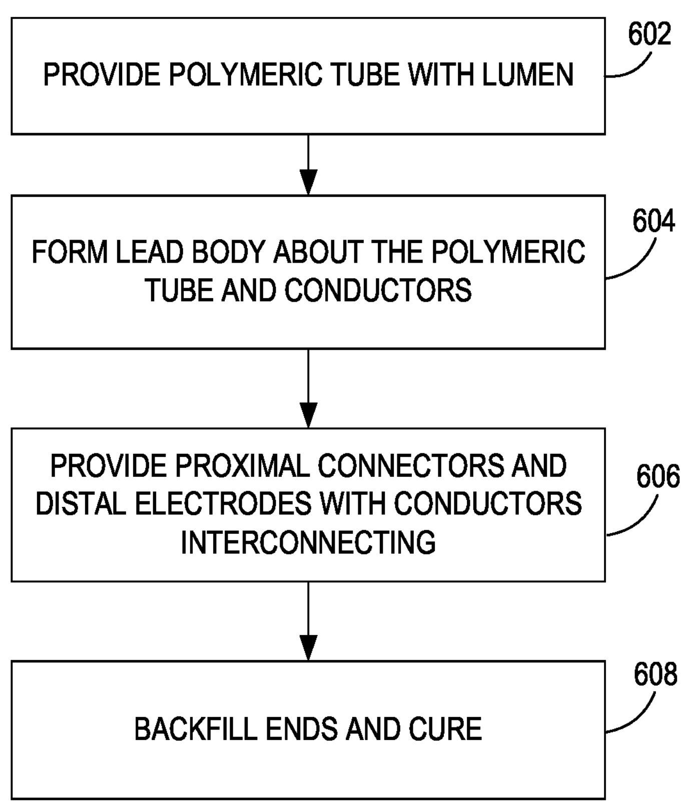
FIG. 16 shows an example of steps of a method to provide a polymeric stylet tube.

A method for creating a lead 106 with the polymeric stylet tube 212 is shown in FIG. 16. Initially, the polymeric tube 212 having the lumen 214 is provided at a step 602. Then, the lead body 202 is formed about the polymeric tube 212 at a step 604, such as by injection molding, reflow of an existing lead body tube that the polymeric tube 212 has been inserted within, and the like. This process may also include encapsulating conductors extending from the proximal to distal end within the lead body 202. The lead body 202 may be formed within the proximal ends and distal ends having an open lumen. Proximal connectors and distal electrodes may then be attached to the lead body 202 and connected to the proximal connectors and distal electrodes at a step 606. The open lumen ends of the lead body 202 may then be backfilled with the desirable material(s) at a step 608 with curing of the backfill materials thereafter.

As discussed above, these examples provide embodiments of a lead, a system that includes the lead, and methods for creating the lead by backfilling the distal end where the lead of these embodiments has improved implantability. The embodiments that include the polymeric stylet tube rather than a metal coil establish pushability of the lead while reducing costs and potential manufacturing defects that may result from the metal coil. The embodiments that include the softer distal backfill material improve the steerability and control for inserting the lead by reducing the whipping action. Thus, embodiments that incorporate both the polymeric stylet tube and the softer distal backfill material achieve the benefits of both.

While embodiments have been particularly shown and described, it will be understood by those skilled in the art that various other changes in the form and details may be made therein without departing from the spirit and scope of the invention.

What is claimed is:

1. An implantable medical lead, comprising:

a lead body defining a first lumen, the lead body comprising a first material;

a polymeric tube that is located within the first lumen, wherein the polymeric tube defines a second lumen and a polymeric tube length that extends from a proximal end of the lead body to a distal end of the lead body, wherein the polymeric tube comprises a second material that extends along the polymeric tube length, the second material having a second durometer rating higher than 60 on a Shore D hardness test, wherein the second durometer rating of the second material is higher than a first durometer rating of the first material, and wherein a center of the second lumen of the polymeric tube is offset relative to a center of the first lumen of the lead body;

at least one proximal connector located on the proximal end of the lead body where the polymeric tube is present;

at least one distal electrode located on the distal end of the lead body where the polymeric tube is present; and at least one conductor interconnecting the at least one proximal connector and the at least one distal electrode.

2. The implantable medical lead of claim 1, wherein the polymeric tube extends from a proximal tip to a distal tip of the lead body.

3. The implantable medical lead of claim 1, wherein the second material comprises at least one of polyimide, acrylonitrile butadiene styrene, polyvinylidene fluoride, polycarbonate, polyethylene terephthalate, cellulose acetate, or polyvinyl chloride.

4. The implantable medical lead of claim 1, further comprising a first backfill material within the first lumen and adjacent the polymeric tube.

5. The implantable medical lead of claim 4, wherein the at least one conductor passes through the first backfill material.

6. The implantable medical lead of claim 4, wherein the first backfill material extends until reaching a point along the lead body that is proximal of the at least one distal electrode where the lead body contacts a complete circumference of the polymeric tube.

7. The implantable medical lead of claim 4, wherein the first backfill material has a third durometer rating lower than 100 on the Shore A hardness scale.

8. The implantable medical lead of claim 4, further comprising a second backfill material within the first lumen and surrounding the first backfill material, the first backfill material having a third durometer rating lower than a fourth durometer rating of the second backfill material.

9. The implantable medical lead of claim 8, wherein the second backfill material extends until reaching a point along the lead body that is proximal of the at least one distal electrode where the lead body contacts a complete circumference of the polymeric tube.

10. The implantable medical lead of claim 8, wherein the first backfill material is present between a point distal of the at least one distal electrode to a point proximal of the at least one distal electrode and wherein the second backfill material is present between a point along the lead body that is proximal of the at least one distal electrode where the lead body contacts a complete circumference of the polymeric tube and proximal of the first backfill material.

11. The implantable medical lead of claim 4, further comprising a second backfill material, wherein the first backfill material forms a third lumen and wherein the second backfill material extends through the third lumen.

12. An implantable medical lead, comprising:

a lead body defining a first lumen, the lead body comprising a first material;

a polymeric tube that is located within the first lumen, wherein the polymeric tube defines a second lumen and a polymeric tube length that extends from a proximal end of the lead body to a distal end of the lead body, wherein the polymeric tube comprises a second material that extends along the polymeric tube length, the second material having a second durometer rating higher than 60 on a Shore D hardness test, wherein the second durometer rating of the second material is higher than a first durometer rating of the first material;

a first backfill material within the first lumen and adjacent the polymeric tube;

a second backfill material within the first lumen and surrounding the first backfill material, the first backfill material having a third durometer rating lower than a fourth durometer rating of the second backfill material;

at least one proximal connector located on the proximal end of the lead body where the polymeric tube is present;

at least one distal electrode located on the distal end of the lead body where the polymeric tube is present, wherein the second backfill material extends until reaching a point along the lead body that is proximal of the at least one distal electrode where the lead body contacts a complete circumference of the polymeric tube; and at least one conductor interconnecting the at least one proximal connector and the at least one distal electrode.

13. An implantable medical lead, comprising:

a lead body defining a first lumen, the lead body comprising a first material;

a polymeric tube that is located within the first lumen, wherein the polymeric tube defines a second lumen and a polymeric tube length that extends from a proximal end of the lead body to a distal end of the lead body, wherein the polymeric tube comprises a second material that extends along the polymeric tube length, the second material having a second durometer rating higher than 60 on a Shore D hardness test, wherein the second durometer rating of the second material is higher than a first durometer rating of the first material;

a first backfill material within the first lumen and adjacent the polymeric tube;

a second backfill material, wherein the first backfill material forms a third lumen and wherein the second backfill material extends through the third lumen;

at least one proximal connector located on the proximal end of the lead body where the polymeric tube is present;

at least one distal electrode located on the distal end of the lead body where the polymeric tube is present; and at least one conductor interconnecting the at least one proximal connector and the at least one distal electrode.

* * * * *